United States Patent [19]

Tümer

[11] Patent Number: 5,557,108
[45] Date of Patent: Sep. 17, 1996

[54] INTEGRATED SUBSTANCE DETECTION AND IDENTIFICATION SYSTEM

[76] Inventor: Tümay O. Tümer, 107 Sweetwood Ct., Riverside, Calif. 92507

[21] Appl. No.: 490,959

[22] Filed: Jun. 15, 1995

Related U.S. Application Data

[63] Continuation-in-part of Ser. No. 143,417, Oct. 25, 1993, Pat. No. 5,446,288.

[51] Int. Cl.$^6$ .................. G01T 3/00; G01T 1/00
[52] U.S. Cl. .................. 250/390.04; 250/390.02; 250/390.12; 250/391; 250/392
[58] Field of Search .................. 250/390.02, 392, 250/391, 390.12, 390.05, 390.04

[56] References Cited

U.S. PATENT DOCUMENTS

| | | |
|---|---|---|
| 4,300,054 | 11/1981 | Dance et al. |
| 4,536,841 | 8/1985 | Waechter et al. |
| 4,646,068 | 2/1987 | Skala ............... 340/580 |
| 4,766,319 | 8/1988 | Regimand ............... 250/390.05 |
| 4,864,142 | 9/1989 | Gomberg. |
| 4,935,194 | 6/1990 | Verschoore. |
| 5,083,019 | 1/1992 | Spangler. |
| 5,109,691 | 5/1992 | Corrigan et al. |
| 5,135,704 | 8/1992 | Shefer et al. |
| 5,446,288 | 8/1995 | Tumer ............... 250/390.05 |

FOREIGN PATENT DOCUMENTS

| | | | |
|---|---|---|---|
| 58-113842 | 7/1983 | Japan | 250/390.02 |
| 59-114446 | 7/1984 | Japan | 250/390.05 |

OTHER PUBLICATIONS

H. Tominaga et al., *Simultaneous Utilization of Neutrons and γ–rays from* $^{252}$ *Cf for Measurement of Moisture and Density* (1983) 34(1) Int. J. Appl. Radiat. Isot. 429–436.

G. Sh. Pekarskii et al., *A Neutron Method of Determining Water in Scrap Metal* (1976) 42(5) Translated from Zavodskaya Laboratoriya 565.

*Primary Examiner*—Constantine Hannaher
*Attorney, Agent, or Firm*—David G. Beck; Townsend and Townsend and Crew LLP

[57] ABSTRACT

An apparatus and method for non-destructively detecting and identifying narcotics, explosives, and other forms of contraband concealed within a container or otherwise hidden from view. A radioactive source is used in conjunction with both neutron and gamma ray detector arrays. Depending upon the desired accuracy as well as the accessibility to all sides of the container, both back scattered and forward scattered radiation can be measured. Multiple detection systems mounted along different axes allow pseudo three dimensional images of the container in question as well as its contents to be produced.

27 Claims, 4 Drawing Sheets

INTEGRATED SUBSTANCE DETECTION AND IDENTIFICATION SYSTEM

CROSS-REFERENCE TO RELATED APPLICATIONS

This application is a continuation-in-part of application Ser. No. 08/143,417, filed Oct. 25, 1993, now U.S. Pat. No. 5,446,288, incorporated herein by reference for all purposes.

BACKGROUND OF THE INVENTION

Narcotics use has been identified as one of the major social problems of the twentieth century. Another significant social problem which has seen major growth during the last twenty five years is terrorism. Governments have sought to reduce acts of terrorism and the trafficking of narcotics by intensive searching of vessels, airplanes, and all forms of luggage and containers crossing national borders. Unfortunately, such search and seizure tactics have met with limited success.

The major impediment to search and seizure operations is the concealment of narcotics, explosives, and other forms of contraband within luggage, cargo, containers or even the structural elements of a transport vehicle. Often these containers or structural elements are made of metal or some other rigid material which, in order to be searched, must be damaged or destroyed.

Accordingly, there is a need for a non-destructive technique for the detection of narcotics, explosives, and other forms of contraband which may be concealed behind barriers or within a container.

Various techniques have been proposed to detect substances behind metal and other barriers. One such system is described in U.S. Pat. No. 4,864,142. That system utilizes the well-known phenomena of neutron resonance scattering, i.e., that a particular nuclei has large neutron cross sections for a neutron beam of a particular resonance energy characteristic of the particular nuclei. In that system, a tunable neutron source provides a beam of nuclei having the resonance energy of a nuclei desired to be detected. The source used is described in the patent at col. 10, lines 29–70, and utilizes a proton beam to generate neutrons. Since the protons are charged particles, their energy can be controlled by passing the beam through a controllable potential difference.

Other non-destructive search methods include the use of animals, sniffers, nuclear magnetic resonance, gamma ray scattering, and ultrasonics. Both animals and sniffers are unable to detect contraband in hermetically sealed containers. Gamma rays and NMR are not effective to penetrate metal barriers. Ultrasonics are useful for probing liquid containers but not very effective otherwise.

From the foregoing, it is apparent that a fast and reliable method of non-destructively searching within containers and through rigid barriers is desired.

SUMMARY OF THE INVENTION

The present invention is an apparatus and method for non-destructive searching and identification of various substances, such as narcotics and explosives, either concealed within containers or hidden behind walls. A relatively weak radioactive source is utilized to provide a flux of fast neutrons and gamma rays. Detector arrays are used to detect scattered thermal neutrons and gamma rays. Gamma rays and neutrons have qualitatively different scattering signatures since neutrons scatter from nuclei and gamma rays generally scatter only from electrons. Thus hydrogen nuclei scatter neutrons effectively, but not gamma rays, while just the opposite is true for heavy atoms. Analysis of both signals allows the identification of the substance in question.

According to one embodiment, two different detection systems are used to identify substances within sealed containers which are transported through the detection systems on a conveyor belt. The first detection system is mounted such that it interrogates the container along its vertical axis while the second detection system is mounted such that it interrogates the container along its horizontal axis. Each detection system is comprised of a neutron and gamma ray source as well as neutron and gamma ray detector arrays. Multiple detector arrays are used to monitor both the back scattered and the forward scattered neutrons and gamma rays. The data from the detector arrays is fed into a microprocessor which analyzes the data from each array to produce four different images of the container and its concealed contents, the four images being displayed on a CRT screen. When suspected contraband is detected, the container is either conveyed to a separate inspection room or the system operator is notified. If desired, the different images can be combined into a single three dimensional view of the container and its contents.

In an alternate embodiment, the neutron and gamma ray images can be combined with x-ray imagery to help the system operator more accurately determine the exact location of any detected contraband.

According to another embodiment, only back scattered neutron and gamma ray data is detected. This embodiment is primarily useful in cases in which it is not possible to detect neutron and gamma ray radiation transmitted through the sample in question, for example when attempting to identify material behind a bulkhead in a vessel.

A further understanding of the nature and advantages of the present invention may be realized by reference to the remaining portions of the specification and the drawings.

DESCRIPTION OF SPECIFIC EMBODIMENTS

Figure 1:
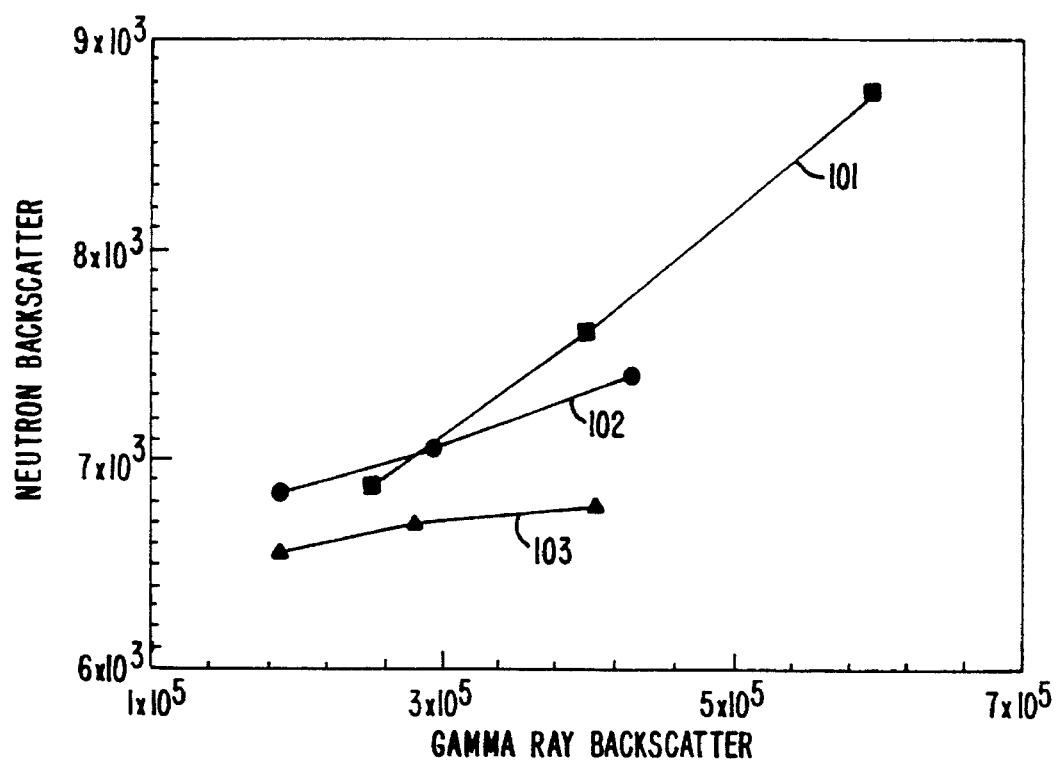
FIG. 1 is a graph of the net gamma ray back scatter count versus the net neutron back scatter count for three different materials.

Gamma rays and neutrons have qualitatively different scattering signatures since neutrons scatter from nuclei and gamma rays generally scatter only from electrons. Hydrogen nuclei will scatter neutrons effectively, but not gamma rays, while just the opposite is true for very heavy atoms. Therefore, for the same material, neutron and gamma ray back scattering produces different but complementary signals. Thus by monitoring the back scatter of both neutrons and gamma rays in a dual signal technique it is possible to determine the identity of concealed material.

Some applications, such as identifying substances hidden behind a wall or other rigid barrier in a vessel, are limited to back scatter techniques. However, detection of narcotics, explosives, and other forms of contraband in luggage, cargo, mail, and other relatively small containers are not limited to detection from one side since all sides of the container are accessible. Therefore, forward scattered radiation can also be used to improve the identification accuracy. The signal from forward scattered neutrons is inversely proportional to the hydrogen content of the material. The signal for forward scattered gamma rays, however, is different. High atomic number (Z) materials absorb gamma rays through the photoelectric effect and therefore decrease the transmitted signal significantly.

Principles of Operation

Neutron back scattering is most effective when neutrons are scattered from the nuclei of light atoms. The slowed, or thermalized, neutrons can then be readily detected by a number of detection schemes. When a neutron collides with an atomic nucleus, it gives the nucleus a kinetic energy $E_R$. This energy is related to the neutron energy, En, by the formula:

$$E_r = [E_n(4A)\cos^2\theta]/[1+A]^2 \qquad (1)$$

where A is the atomic mass number and $\theta$ is the angle of recoil of the neutron. If A is small, for example A=1 (i.e., hydrogen), the neutron can lose up to 100% of its kinetic energy in the interaction, resulting in many effectively thermalized, back scattered neutrons. In contrast, if A>>1 the neutron loses little energy and very few thermalized neutrons result. Once the neutrons are thermalized they can be easily detected. Typically a narcotic contains approximately 6 to 9 percent by weight of hydrogen; such a large hydrogen content produces a relatively high flux of back scattered thermal neutrons.

Equation 1 shows that the energy given to the recoil nucleus is uniquely determined by the scattering angle. If the neutron is incident at a grazing angle it will be deflected only slightly and the recoil nucleus is emitted perpendicular to the neutron direction ($\theta \approx 90°$). At the other extreme, a head-on collision of the incoming neutron with the target nucleus will lead to a recoil in the same direction ($\theta \approx 0°$), resulting in the maximum possible recoil energy, or $$[E_R]_{max} = 4AE_n/[1+A]^2 \qquad (2)$$

Equation 2 shows that the recoil energy is strongly dependent on the atomic mass of the recoil nucleus. Table 1 lists the maximum fraction of the incoming neutron energy that can be transferred to a recoil nucleus in a single collision for a variety of target nuclei. As indicated, the energy transferred to the nucleus decreases rapidly with increasing A. Therefore, many more collisions will be required to thermalize and stop a neutron for materials with large atomic mass.

TABLE 1

| Target Nucleus | A | $[E_R/E_n]_{max}=4A/(1+A)^2$ |
|---|---|---|
| $^1H_1$ | 1 | 1 |
| $^2H_1$ | 2 | 0.889 |
| $^3He_2$ | 3 | 0.750 |
| $^4He_2$ | 4 | 0.640 |
| $^{12}C_6$ | 12 | 0.284 |
| $^{16}O_8$ | 16 | 0.221 |

The neutron forward scatter signal complements the back scatter signal. Hydrogen rich materials reduce neutron forward scatter by thermalizing neutrons and back scattering them.

Gamma rays (high energy photons) interact with matter usually in one of three ways; by the photoelectric effect, by Compton scattering, or by pair production. Only Compton scattering produces back scattered gamma rays, the photon is otherwise absorbed. Gamma rays emitted from common radioisotope sources have energies ranging from 50 keV to 5 MeV, energies where Compton scattering is the most dominant interaction. In Compton scattering, the gamma ray scatters from electrons not nuclei, and the incoming gamma ray photon is deflected, transferring a portion of its energy to the recoil electron which is assumed initially to be at rest. The scattered photon energy $E_\gamma^S$, obtained from energy and momentum conservation laws, is given in terms of the incident photon energy $E_\gamma$ and the scattering angle $\theta$ by $$E_\gamma^S = E_\gamma/[1+(E_\gamma/E_0)(1-\cos\theta)] \qquad (3)$$

where $E_0$ is the electron rest mass energy (0.511 MeV). For small angle scattering very little energy is transferred to the electron. A back scattered photon, where $\theta=\pi$ will have the least energy. However, for gamma ray energies much smaller than 0.511 MeV the back scattered photon keeps most of the incident energy.

The probability of Compton scattering depends on the density of electrons and therefore increases linearly with the atomic number Z of the scatterer. The angular distribution of scattered gamma rays can be calculated from the Klein-Nishina formula, which is well known by those skilled in the art. It shows a strong tendency for forward scattering at high gamma ray energies, $E_\gamma>300$ keV, while at lower energies the back scattering probability increases with decreasing energy. Therefore, only gamma rays with energies in the region of 50 to 300 keV can be used effectively for back scatter measurements. For high Z (Z>20) materials such as steel and especially lead, the photoelectric effect becomes the important process below about 200 KeV and the low energy gamma rays are readily absorbed. Therefore, the gamma ray back scatter signal for gamma rays between 50 to 200 keV is significantly different for different materials and depends strongly on the atomic number Z.

The forward scattered gamma ray signal is not a true complement of the back scattered signal. For example, high Z materials will absorb low energy gamma rays. Therefore, both the back scattered and the forward scattered gamma ray signals will decrease. This unique property of the gamma ray signal will provide different but complementary additional information when both the back scattered and the forward scattered signals are used.

Back Scatter Data

Preliminary back scatter data was obtained using $^{241}$AmBe and $^{252}$Cf neutron sources in conjunction with a 5 centimeter $^6$LiI(Eu) crystal mounted on a photomultiplier tube. To obtain back scatter data the sources were placed next to the $^6$LiI(Eu) scintillator. One ounce of powdered sugar was placed inside a small envelope to simulate a small amount of a narcotic. The envelope was flattened to evenly distribute the sugar. Similarly two more envelopes were prepared, one with 1 ounce of paper and the other with 1 ounce of aluminum foil. These envelopes were placed 2.5 centimeters from the front of the detector. The simultaneous gamma ray and neutron spectra were obtained for a fixed time period of 200 seconds. This period of time was required due to the low source strength used to obtain this data. Sub-second measurement times can be achieved using higher strength sources. The measurements were repeated with the envelopes 5 centimeters and 7.5 centimeters away from the detector, thereby simulating a scan.

Both gamma ray and neutron back scattering spectra were obtained for each sample. Background, estimated by interpolation, was removed thereby yielding a net gamma ray and a net neutron count rate for each material. FIG. 1 is a graph of the net gamma ray count versus the net neutron count, illustrating a nearly linear relationship for a particular material placed behind a particular panel. Data graph 101 is for the envelop filled with one ounce of powdered sugar, data graph 102 is for the envelop filled with one ounce of paper, and data graph 103 is for the envelop filled with one ounce of aluminum foil. Data graph 101 gives the strongest back scatter signal for both the gamma rays and the neutrons. Data graph 103 gives the lowest back scatter signal, as expected. The slopes of the three sets of data are noticeably different.

Forward Scatter Data

Figure 2:
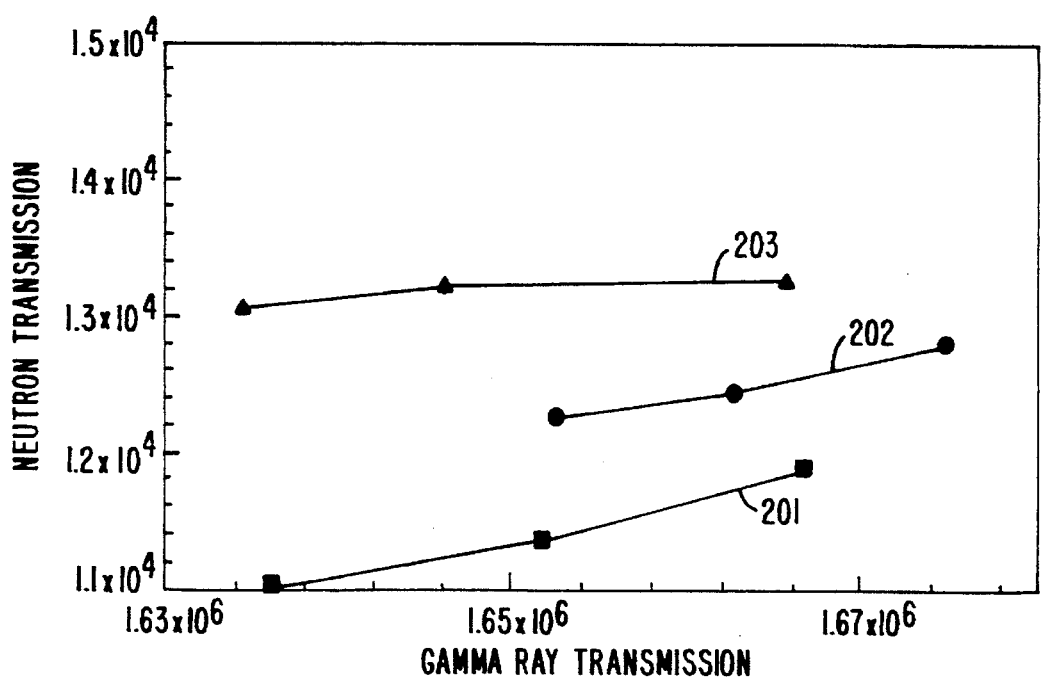
FIG. 2 is a graph of the reduction in forward scattered gamma ray radiation versus the reduction in forward scattered neutron radiation for three different material.

The $^{241}$AmBe and the $^{252}$Cf sources were placed opposite the $^6$LiI(Eu) scintillator and the envelope was put between the scintillator and the sources. As in the back scatter study, powdered sugar, paper, and aluminum were used. In this study, 1, 2, and 3 ounces of each of the materials were placed inside the envelopes. FIG. 2 is a graph of the net gamma ray count versus the net neutron count for the different materials. Data graph 201 is associated with the powdered sugar, data graph 202 is associated with the paper, and data graph 203 is associated with the aluminum foil. In FIG. 2, the "signal" is a reduction in the strength of the forward scattered radiation, not an increase. Data graph 201 showed the strongest signal.

Neutron and Gamma Ray Separation

The scintillation efficiency of $^6$LiI(Eu) scintillators is nearly the same for both electrons and heavily charged particles. A 4.1 MeV electron will yield about the same light as the 4.78 MeV $^6$Li reaction products. Therefore, low energy back scattered gamma rays from 50 to 200 keV produce a pulse height approximately proportional to the energy of the gamma ray (for photoelectric absorption), whereas each thermal neutron interaction will produce a pulse equivalent to 4.1 MeV on the same scale.

Figure 3:
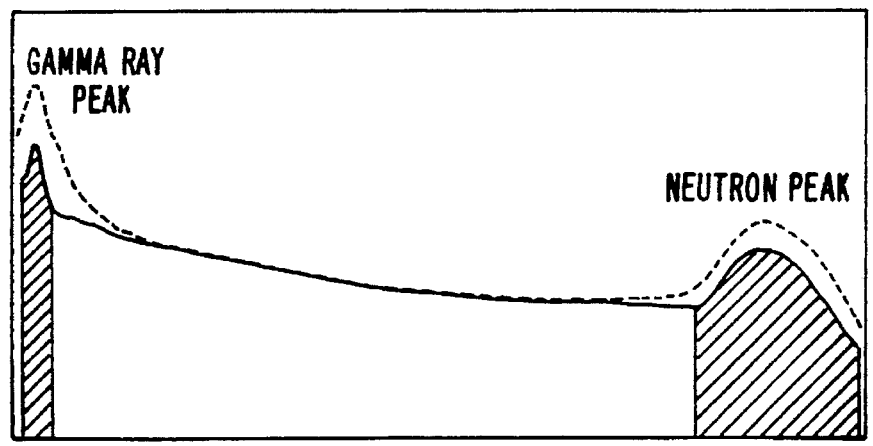
FIG. 3 is an illustration of the simultaneously back scattered neutron and gamma ray pulse height spectrum from 80 ounces of powdered sugar, the sugar simulating a narcotic, along with the pulse height spectrum from the source alone.

FIG. 3 is an illustration of the simultaneously back scattered neutron and gamma ray pulse height spectrum from 80 ounces of powdered sugar along with the pulse height spectrum from the $^{241}$AmBe source alone. The powdered sugar was used to simulate organic materials such as drugs. The source alone background peaks are shaded. The Y-axis is based on a logarithmic scale and shows the counts per channel. The peak on the left is due to back scattering of the 60 keV gamma ray line from the $^{241}$AmBe source while the peak on the right is due to thermal neutrons from the same source detected by the same $^6$LiI(Eu) detector. The neutron and gamma ray peaks are well separated and the region in between the two peaks is uniform and not influenced by either the back scattered neutrons or gamma rays. Therefore, a clear separation of the two different signals can be achieved without loss of any portion of the signal using simple pulse height discrimination.

A 2 millimeter thick $^6$LiI(Eu) crystal is 99% efficient in absorbing both 50 keV gamma rays and thermal neutrons. Therefore, $^{241}$AmBe is a good choice for a gamma ray signal.

Hand Held Inspection System

Figure 4:
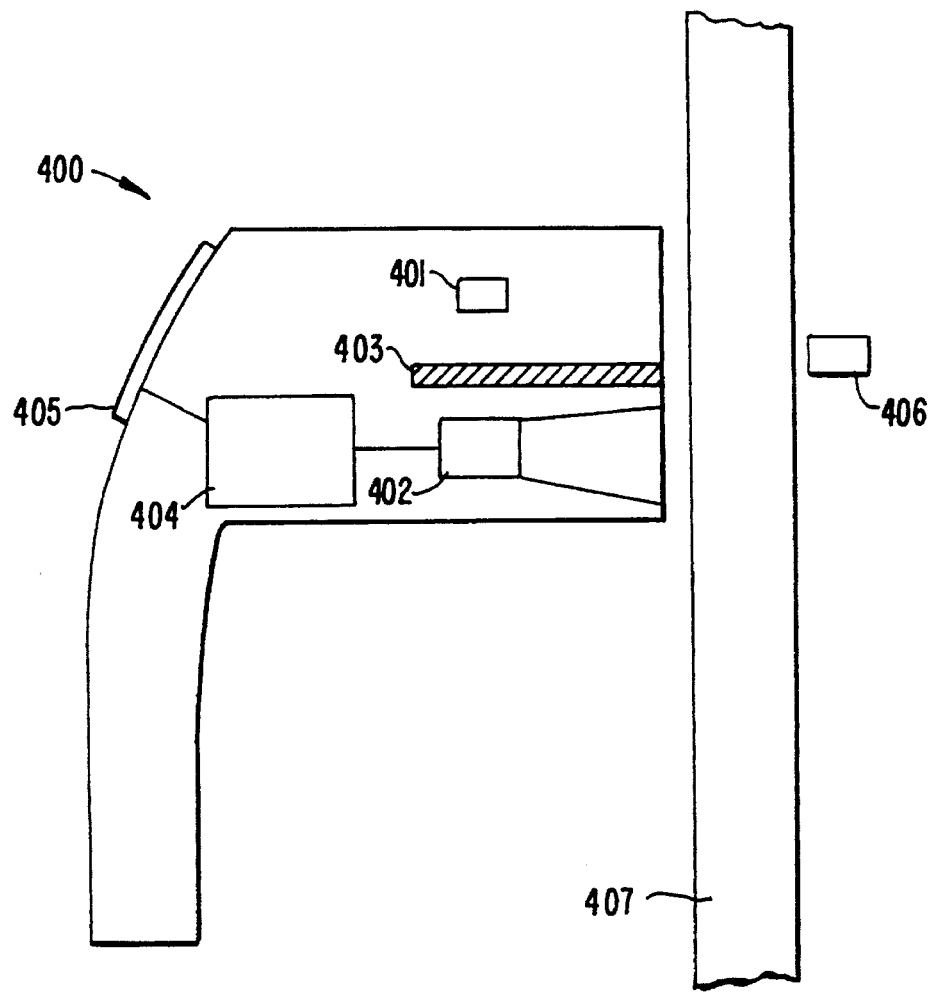
FIG. 4 is an illustration of a portable system of identifying substances based on back scattered neutron and gamma ray radiation.

FIG. 4 is an illustration of a portable embodiment of the present invention which can be used to identify substances based solely on back scattered data. In the preferred embodiment a portable system 400 contains a single, self-contained, radioactive source of neutrons and gamma rays 401 positioned alongside a single detector 402 which is capable of detecting both neutrons and gamma rays. Separating source 401 and detector 402 is a shield 403. Shield 403 prevents detector 402 from directly viewing source 401. Contained within system 400 is a microprocessor 404 and a display 405. The output of detector 402 is analyzed by microprocessor 404. The output of microprocessor 404 can be presented to the user on display 405 in a variety of formats, depending upon the application. In the preferred embodiment, microprocessor compares the back scattered neutron and gamma ray radiation to a list of known substances 406 which the user suspects may be concealed behind wall 407. When a match is found, the identity of the concealed substance is displayed on display 405. In an alternate embodiment, the flux of back scattered neutrons and gamma rays detected by detector 402 is displayed on display 405.

Figure 5:
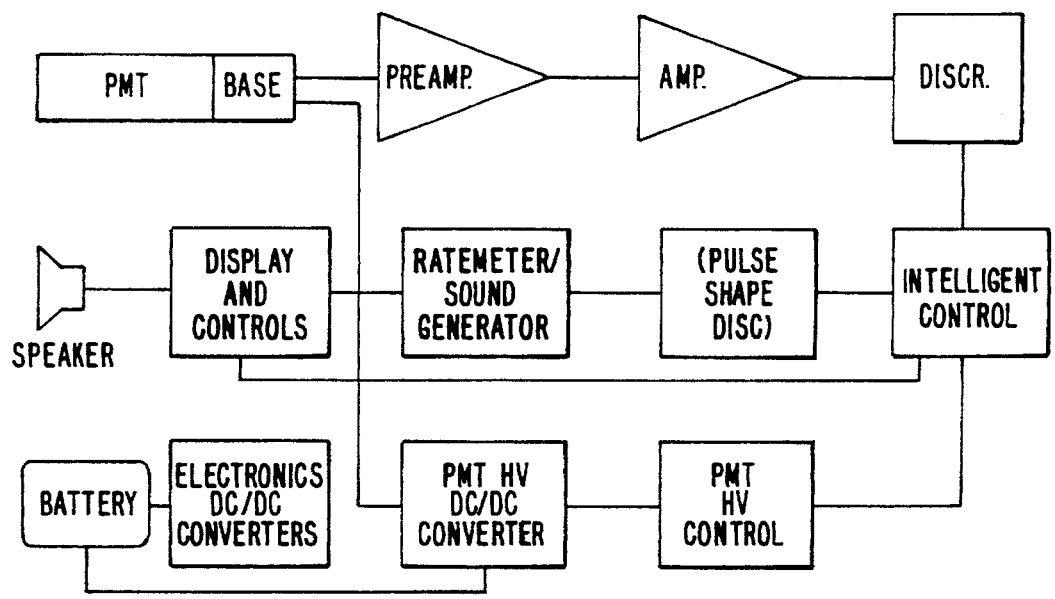
FIG. 5 is a block diagram of detector electronics for the embodiment shown in FIG. 4.

A block diagram of the detector electronics for this embodiment is depicted in FIG. 5. The circuit includes preamplifier, amplifier (possibly with pulse shaping), discriminator, intelligent control, rate meter, display, and operator control. A microcomputer is utilized for data analysis. Battery and DC/DC convertors for the electronics power supply and PMT high voltage power supplies can be located inside the detector housing.

Three Dimensional Inspection System

In the preferred embodiment of the present invention, a combination of two different detection systems are used to identify substances within sealed containers. Each detection system includes detector arrays to measure the gamma ray back scatter, gamma ray forward scatter, neutron back scatter, and neutron forward scatter for each substance in question which, when collectively analyzed, provide the necessary analysis information.

Figure 6:
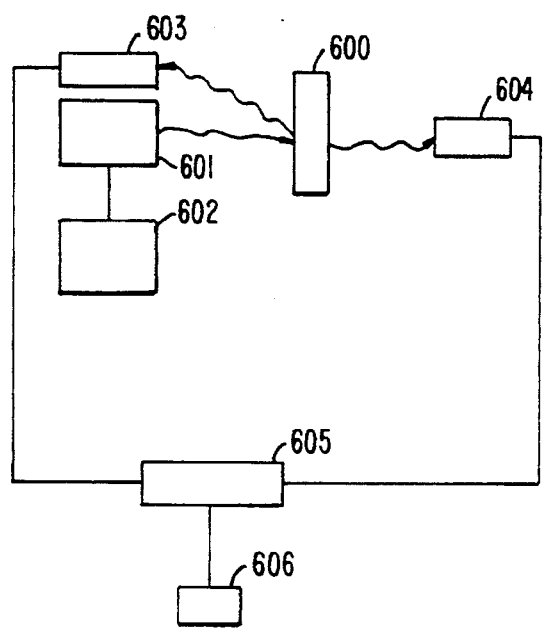
FIG. 6 is an illustration of a functional block diagram for the preferred embodiment of a three dimensional substance identification system.

FIG. 6 is an illustration of a functional diagram for the preferred embodiment. A container 600 is placed in close proximity to a source of neutrons and gamma rays 601. Source 601 is powered hy high voltage source 602. A detector 603 detects both back scattered gamma rays and neutrons. Similarly, a detector 604 detects both forward scattered gamma rays and neutrons. The output spectra from detectors 603 and 604 is sent to a microprocessor 605 for data analysis. Microprocessor 605 is coupled to a display 606. The distance between detectors 603 and 604 and container 600 can he changed during testing in order to provide microprocessor 605 with additional data to aid in the identification of substances within container 600.

Figure 7:
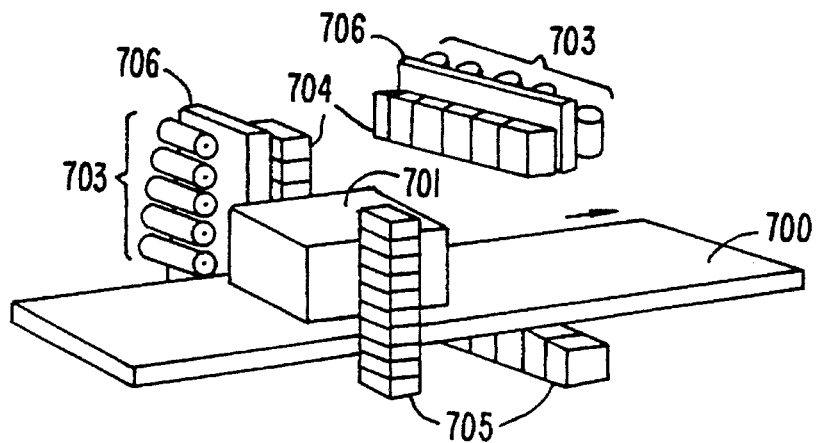
FIG. 7 is an illustration of a three dimensional detection system according to the present invention integrated into a conveyer-type luggage transportation or sorting system.

FIG. 7 is an illustration of a three dimensional detection system according to the present invention integrated into a conveyer-type luggage transportation or sorting system. A conveyer belt 700 is used to transport a container 701 through the detection system. Conveyer belt 700 may he part of a luggage transport system such as those used at major airport terminals, or it may he part of a stand alone inspection system. The speed of the conveyer system depends primarily on the strength of the neutron and gamma ray source. The detectors can be designed with sub-second response times.

Container 700 is transported through two different detector systems, a first system mounted along the container's horizontal axis and a second system mounted along the container's vertical axis. Both detector systems are comprised of a neutron and gamma ray source 703, a back scatter detector array 704, and a forward scatter detector array 705. Sources 703 are separated from back scatter detector arrays 704 by a shield 706.

In the preferred embodiment, detector arrays 704 and 705 are linear arrays of individual detectors of approximately a few square centimeters each, thereby producing images with similar resolution. If higher resolution is required smaller detectors can be used. Arrays 704 and 705 need not he two dimensional arrays since container 700 passes through the arrays. In an alternate embodiment in which the operator simply places the container to be examined within the detection system and the container is not moved during examination, two dimensional arrays are required.

In the preferred embodiment, sources 703 produce both the neutron and gamma rays. Although a single point source can be used, typically sources 703 are either line sources or arrays of similar sources placed within a moderator.

Two Dimensional Inspection System

Figure 8:
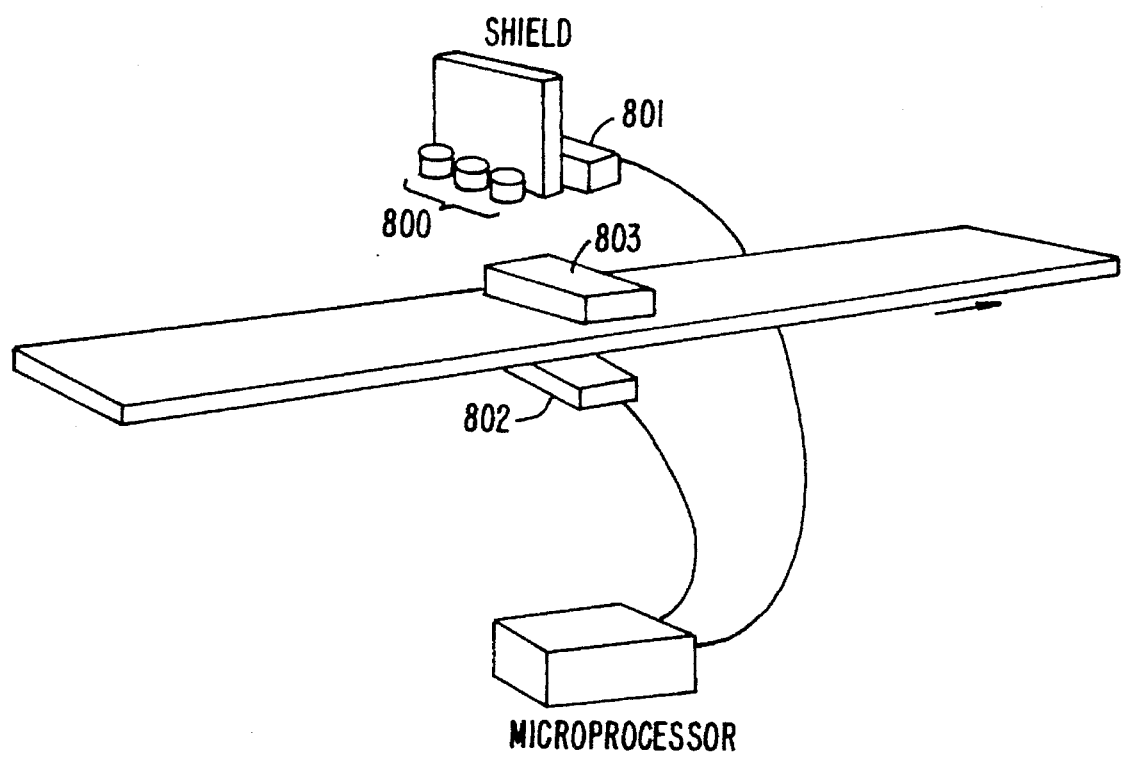
FIG. 8 is an illustration of an embodiment of the present invention utilizing two dimensional inspection.

FIG. 8 is an illustration of an embodiment of the present invention utilizing two dimensional inspection. This embodiment is similar to that shown in FIG. 7 except that only a single source 800 is used in conjunction with a single back scatter detector array 801 and a single forward scatter detector array 802 to image container 803. Source 8! 00 is typically either a line source or an array of similar sources.

Data Acquisition and Analyis

In the preferred embodiment, the output of the detectors is fed into a microprocessor. The data analysis performed by the microprocessor as well as the final form of the output is dependent upon the application.

In the preferred embodiment of the invention, the microprocessor analyzes the detector data taken from each detector array. Assuming the system only includes one neutron source and one gamma ray source, the system produces four different images which can then be displayed on a CRT screen. Thus there are two back scatter images as wells as two images from the forward scatter detector arrays. Each image is normalized and color coded, the color coding representing signal intensity. In one embodiment, the CRT screenis divided into four quadrants, each quadrant showing a different image of the container. If multiple source systems are used, for example to provide three dimensional imaging as described above, then more than four images can be produced and displayed.

In another embodiment of the invention, the multiple images of the container under inspection as well as its contents can be combined into a variety of different two dimensional projections. For example, if two orthogonally positioned inspection systems are used, the system has access to eight different sets of data; four sets of back scatter data and four sets of forward scatter data. Thus pseudo-three dimensional views of the container and its contents can be constructed as well as a variety of other combined images (e.g., combination of all neutron scatter data, combination of all gamma ray scatter data, combination of all forward scatter data, etc.).

In another embodiment of the invention, the microprocessor analyzes the data taken from each detector array, comparing the signature of every object within the container to a user input list of harmful or potentially dangerous materials. For example, the list of materials could include the signature of known narcotics and explosives. After a potentially dangerous material has been identified, the system can either be programmed to alert a system operator so that the operator can review the data or the system can simply divert the container from its normal route into a special inspection area.

In another embodiment, the back scatter and forward scatter apparatus of the present invention is combined with a conventional x-ray imager. By superimposing the x-ray imagery with the neutron and gamma ray data, identification of suspected articles within the container being inspected is further simplified. For example, the x-ray data may show a simple pair of shoes within a piece of luggage while the neutron and gamma ray data may show that the shoes have the signature of a known narcotic such as heroin. By combining the two sets of data the system operator knows to carefully inspect the shoes looking for false heels, etc.

In another embodiment of the invention, the system utilizes the energy spectrum detected by one or more individual detectors within one or more of the detector arrays. Separate detector arrays to measure the energy spectrum can also be used. The use of energy spectrums further enhances the ability to correctly identify the concealed substances in question. The energy spectrum data can either be used by the system operator, or automatically used by the system in locating and identifying concealed substances. In one embodiment, the output of the individual detectors is color coded according to the measured energy spectra. Color coding allows the energy spectrum data to be easily and clearly presented to a user as a color coded image of the container and its contents.

In another embodiment of the invention, whenever the system identifies suspected contraband, the system provides the user with an identification confidence rating. For example, the system may determine that there is a 95 percent probability that a piece of luggage contains cocaine at one location and a 65 percent probability that the same piece of luggage contains plastic explosives at a second location.

As will be understood by those familiar with the art, the present invention may be embodied in other specific forms without departing from the spirit or essential characteristics thereof. Accordingly, disclosure of the preferred embodiment of the invention is intended to be illustrative, but not limiting, of the scope of the invention which is set forth in the following claims.

I claim:

1. A method for identifying substances disposed behind a barrier having a front, said method comprising the steps of:

positioning a radioactive source on the front side of the barrier, said source providing a flux of gamma rays and fast neutrons;

positioning a detector near said source, said detector capable of measuring a flux of scattered gamma rays and generating a gamma ray output signal corresponding to a magnitude of said scattered gamma rays, and said detector capable of measuring a flux of scattered neutrons and generating a neutron output signal corresponding to a magnitude of said scattered neutrons; and comparing the magnitude of said detector output signals to determine the identity of substances disposed behind said barrier.

2. A method for identifying substances disposed behind a barrier having a front, said method comprising the steps of:

positioning a first source on the front side of the barrier, said first source providing a flux of gamma rays;

positioning a first detector near said first source, said first detector capable of measuring a flux of scattered gamma rays and generating a gamma ray output signal corresponding to a magnitude of said scattered gamma rays;

positioning a second source proximate to said first source on the front side of the barrier, said second source providing a flux of neutrons;

positioning a second detector near said second source, said second detector capable of measuring a flux of scattered neutrons and generating a neutron output signal corresponding to a magnitude of said scattered neutrons; and comparing said first detector output signal and said second detector output signal to determine the identity of substances disposed behind said barrier.

3. A system for identifying substances behind a surface, comprising:

a radioactive source for providing a flux of gamma rays and fast neutrons;

a detector proximate to said radioactive source, said detector measuring a flux of scattered gamma rays and generating a gamma ray output signal corresponding to a magnitude of said scattered gamma rays, and said detector measuring a flux of scattered neutrons and generating a neutron output signal corresponding to a magnitude of said scattered neutrons; and an output device, coupled to said detector, for converting said detector output signals to a format indicating the identity of said substances located behind said surface.

4. A method for identifying substances disposed within a container, said container having a first side, a second side, a top, and a bottom, said method comprising the steps of:

positioning a source of neutrons on the first side of the container;

positioning a source of gamma rays on the first side of the container;

positioning a first detector array near said source of neutrons, said first detector array capable of measuring a magnitude of back scattered neutrons at a plurality of locations and generating a first plurality of output signals corresponding to said magnitude of back scattered neutrons;

positioning a second detector array near said source of gamma rays, said second detector array capable of measuring a magnitude of back scattered gamma rays at said plurality of locations and generating a second plurality of output signals corresponding to said magnitude of back scattered gamma rays;

positioning a third detector array on the second side of the container and opposite said source of neutrons, said third detector array capable of measuring a magnitude of forward scattered neutrons at said plurality of locations and generating a third plurality of output signals corresponding to said magnitude of forward scattered neutrons;

positioning a fourth detector array on the second side of the container and opposite said source of gamma rays, said fourth detector array capable of measuring a magnitude of forward scattered gamma rays at said plurality of locations and generating a fourth plurality of output signals corresponding to said magnitude of forward scattered gamma rays; and analyzing said first, second, third, and fourth pluralities of output signals to identify substances disposed within the container.

5. The method of claim 4, further comprising the steps of:

positioning a second source of neutrons on the top side of the container;

positioning a second source of gamma rays on the top side of the container;

positioning a fifth detector array near said second source of neutrons, said fifth detector array capable of measuring a magnitude of back scattered neutrons at a plurality of locations and generating a fifth plurality of output signals corresponding to said magnitude of back scattered neutrons;

positioning a sixth detector array near said second source of gamma rays, said sixth detector array capable of measuring a magnitude of back scattered gamma rays at said plurality of locations and generating a sixth plurality of output signals corresponding to said magnitude of back scattered gamma rays;

positioning a seventh detector array on the bottom side of the container and opposite said second source of neutrons, said seventh detector array capable of measuring a magnitude of forward scattered neutrons at said plurality of locations and generating a seventh plurality of output signals corresponding to said magnitude of forward scattered neutrons;

positioning a eighth detector array on the bottom side of the container and opposite said second source of gamma rays, said eighth detector array capable of measuring a magnitude of forward scattered gamma rays at said plurality of locations and generating a eighth plurality of output signals corresponding to said magnitude of forward scattered gamma rays; and analyzing said fifth, sixth, seventh, and eighth pluralities of output signals to identify substances disposed within the container.

6. The method of claim 5, further comprising the steps of:

conveying the container from a first position to a second position, wherein at said first position said first and second sources of neutrons and said first and second sources of gamma rays are positioned at a leading edge of the container, and wherein at said second position said first and second sources of neutrons and said first and second sources of gamma rays are positioned at a trailing edge of the container;

forming a first image of said container and said substances disposed within said container from the plurality of output signals from said first detector array;

forming a second image of said container and said substances disposed within said container from the plurality of output signals from said second detector array;

forming a third image of said container and said substances disposed within said container from the plurality of output signals from said third detector array;

forming a fourth image of said container and said substances disposed within said container from the plurality of output signals from said fourth detector array;

forming a fifth image of said container and said substances disposed within said container from the plurality of output signals from said fifth detector array;

forming a sixth image of said container and said substances disposed within said container from the plurality of output signals from said sixth detector array;

forming a seventh image of said container and said substances disposed within said container from the plurality of output signals from said seventh detector array;

forming a eighth image of said container and said substances disposed within said container from the plurality of output signals from said eighth detector array; and combining said first, second, third, fourth, fifth, sixth, seventh, and eighth images to form a pseudo three dimensional image of said container and said substances contained within said container.

7. The method of claim 6, further comprising the step of combining images to form a composite image, said images selected from the group consisting of said first image, said second image, said third image, said fourth image, said fifth image, said sixth image, said seventh image, and said eighth image.

8. The method of claim 4, wherein a single source provides said neutrons and said gamma rays.

9. The method of claim 8, wherein said single source is a line source.

10. The method of claim 4, wherein a single detector array functions as said first detector array and as said second detector array.

11. The method of claim 4, further comprising the step of conveying the container from a first position to a second position, wherein at said first position said source of neutrons and said source of gamma rays are positioned at a leading edge of the container, and wherein at said second position said source of neutrons and said source of gamma rays are positioned at a trailing edge of the container.

12. The method of claim 11, further comprising the steps of:

forming a first image of said container and said substances disposed within said container from the plurality of output signals from said first detector array;

forming a second image of said container and said substances disposed within said container from the plurality of output signals from said second detector array;

forming a third image of said container and said substances disposed within said container from the plurality of output signals from said third detector array; and forming a fourth image of said container and said substances disposed within said container from the plurality of output signals from said fourth detector array.

13. The method of claim 12, further comprising the step of combining images to form a composite image, said images selected from the group consisting of said first image, said second image, said third image, and said fourth image.

14. The method of claim 13, further comprising the steps of:

positioning a source of x-rays on the first side of the container;

positioning an x-ray detector array on the second side of the container and opposite said source of x-rays, said x-ray detector array capable of measuring a flux of x-rays at said plurality of locations and generating a plurality of output signals corresponding to said flux of x-rays;

generating an x-ray image of said container and said substances disposed within said container; and combining said x-ray image and said composite image to form a single image of said container and said substances disposed within said container.

15. The method of claim 4, wherein said analyzing step further comprises the steps of:

comparing said first plurality of output signals to a lookup table of known neutron back scatter characteristics for a plurality of preselected substances;

comparing said second plurality of output signals to a lookup table of known gamma ray back scatter characteristics for said plurality of preselected substances;

comparing said third plurality of output signals to a lookup table of known neutron forward scatter characteristics for said plurality of preselected substances; and comparing said fourth plurality of output signals to a lookup table of known gamma ray forward scatter characteristics for said plurality of preselected substances.

16. The method of claim 4, further comprising the steps of:

selecting at least one detector from the group of detector arrays consisting of said first, second, third, and fourth detector arrays;

determining an energy spectrum, said energy spectrum measured by said selected detector; and anaylzing said energy spectrum to identify said substances disposed within the container.

17. The method of claim 4, wherein said substances disposed within said container are identified as either non-contraband substances or contraband substances.

18. A system for identifying substances within a container, said container having a first side, a second side, a top, and a bottom, said system comprising:

a source of neutrons positioned on the first side of the container;

a source of gamma rays positioned on the first side of the container;

a first detector array proximate said source of neutrons, said first detector array capable of measuring a magnitude of back scattered neutrons at a plurality of locations and generating a first plurality of output signals corresponding to said magnitude of back scattered neutrons;

a second detector array proximate said source of gamma rays, said second detector array capable of measuring a magnitude of back scattered gamma rays at said plurality of locations and generating a second plurality of output signals corresponding to said magnitude of back scattered gamma rays;

a third detector array on the second side of the container and opposite said source of neutrons, said third detector array capable of measuring a magnitude of forward scattered neutrons at said plurality of locations and generating a third plurality of output signals corresponding to said magnitude of forward scattered neutrons;

a fourth detector array on the second side of the container and opposite said source of gamma rays, said fourth detector array capable of measuring a magnitude of forward scattered gamma rays at said plurality of locations and generating a fourth plurality of output signals corresponding to said magnitude of forward scattered gamma rays; and a first computer coupled to said first, second, third, and fourth detector arrays, said first computer analyzing said output signals to identify substances disposed within the container.

19. The system of claim 18, further comprising:

a second source of neutrons on the top side of the container;

a second source of gamma rays on the top side of the container;

a fifth detector array proximate said second source of neutrons, said fifth detector array capable of measuring a magnitude of back scattered neutrons at a plurality of locations and generating a fifth plurality of output signals corresponding to said magnitude of back scattered neutrons;

a sixth detector array proximate said second source of gamma rays, said sixth detector array capable of measuring a magnitude of back scattered gamma rays at said plurality of locations and generating a sixth plurality of output signals corresponding to said magnitude of back scattered gamma rays;

a seventh detector array on the bottom side of the container and opposite said second source of neutrons, said seventh detector array capable of measuring a magnitude of forward scattered neutrons at said plurality of locations and generating a seventh plurality of output signals corresponding to said magnitude of forward scattered neutrons;

a eighth detector array on the bottom side of the container and opposite said second source of gamma rays, said eighth detector array capable of measuring a magnitude of forward scattered gamma rays at said plurality of locations and generating a eighth plurality of output signals corresponding to said magnitude of forward scattered gamma rays; and a second computer coupled to said fifth, sixth, seventh, and eighth detector arrays, said second computer analyzing said output signals to identify substances disposed within the container.

20. The system of claim 19, wherein said second computer and said first computer are the same computer.

21. The system of claim 18, wherein said source of neutrons and said source of gamma rays are the same source.

22. The system of claim 18, wherein said first detector array and said second detector array are the same detector array.

23. The system of claim 18, further comprising a conveying device for conveying the container from a first position to a second position, wherein at said first position said source of neutrons and said source of gamma rays are positioned at a leading edge of the container, and wherein at said second position said source of neutrons and said source of gamma rays are positioned at a trailing edge of the container.

24. The system of claim 23, wherein said first computer forms a first image of said container and said substances disposed within said container from the plurality of output signals from said first detector array, a second image of said container and said substances disposed within said container from the plurality of output signals from said second detector array, a third image of said container and said substances disposed within said container from the plurality of output signals from said third detector array, and a fourth image of said container and said substances disposed within said container from the plurality of output signals from said fourth detector array, and wherein said first, second, third, and fourth images are displayed on a display screen coupled to said first computer.

25. The system of claim 24, wherein said first computer forms a composite image of said container and said substances disposed within said container by combining images selected from the group consisting of said first image, said second image, said third image, and said fourth image, and wherein said composite image is displayed on said display screen.

26. The system of claim 25, further comprising:

a source of x-rays proximate the first side of the container;

an x-ray detector array on the second side of the container and opposite said source of x-rays, said x-ray detector array capable of measuring a flux of x-rays at said plurality of locations and generating a plurality of output signals corresponding to said flux of x-rays; and wherein said first computer is coupled to said x-ray detector array, said first computer generating an x-ray image of said container and said substances disposed within said container, and wherein said display screen displays said x-ray image simultaneously with said composite image.

27. A method for identifying substances disposed within a container, said container atop a conveying device, said method comprising the steps of:

positioning a source of neutrons and gamma rays above said conveying device;

positioning a first detector proximate to said source, said first detector capable of measuring a flux of back scattered neutrons and back scattered gamma rays and generating an output signal corresponding to said flux of back scattered neutrons and an output signal corresponding to said flux of back scattered gamma rays;

positioning a second detector below said conveying device and opposite said source, said second detector capable of measuring a flux of forward scattered neutrons and forward scattered gamma rays and generating an output signal corresponding to said flux of forward scattered neutrons and an output signal corresponding to said flux of forward scattered gamma rays;

conveying said container between said first detector and said second detector; and analyzing said output signals to identify said substances within said container.

\* \* \* \* \*

UNITED STATES PATENT AND TRADEMARK OFFICE
CERTIFICATE OF CORRECTION

PATENT NO. : 5,557,108
DATED : Sept. 17, 1996
INVENTOR(S) : Tümay O. Tümer

It is certified that error appears in the above-identified patent and that said Letters Patent is hereby corrected as shown below:

At column 1, line 3, insert the following:

GOVERNMENT RIGHTS NOTICE

-- This invention was made with U.S. Government support under Contract Number DTRS-57-91-C-00004, awarded by the Department of Transportation. The U.S. Government has certain rights in the invention.--

Signed and Sealed this

Sixth Day of October, 1998

BRUCE LEHMAN

*Attest:*

*Attesting Officer*    Commissioner of Patents and Trademarks